(12) United States Patent
Chaudhary

(10) Patent No.: US 9,233,133 B2
(45) Date of Patent: Jan. 12, 2016

(54) DETOXIFIER HERBAL FORMULATION

(76) Inventor: Manu Chaudhary, Panchkula (IN)

( * ) Notice: Subject to any disclaimer, the term of this patent is extended or adjusted under 35 U.S.C. 154(b) by 0 days.

(21) Appl. No.: 13/881,473

(22) PCT Filed: Oct. 25, 2011

(86) PCT No.: PCT/IN2011/000744
§ 371 (c)(1),
(2), (4) Date: Jun. 6, 2013

(87) PCT Pub. No.: WO2012/056476
PCT Pub. Date: May 3, 2012

(65) Prior Publication Data
US 2014/0147394 A1    May 29, 2014

(30) Foreign Application Priority Data
Oct. 25, 2010 (IN) .......................... 2545/DEL/2010

(51) Int. Cl.
| | | |
|---|---|---|
| *A01N 65/00* | (2009.01) |
| *A61K 36/28* | (2006.01) |
| *A61K 36/00* | (2006.01) |
| *A61K 36/185* | (2006.01) |
| *A61K 36/19* | (2006.01) |
| *A61K 36/29* | (2006.01) |
| *A61K 36/59* | (2006.01) |
| *A61K 36/74* | (2006.01) |
| *A61K 36/24* | (2006.01) |
| *A61K 36/48* | (2006.01) |
| *A61K 36/482* | (2006.01) |
| *A61K 36/888* | (2006.01) |
| *A61K 9/00* | (2006.01) |

(52) U.S. Cl.
CPC .............. *A61K 36/28* (2013.01); *A61K 36/00* (2013.01); *A61K 36/185* (2013.01); *A61K 36/19* (2013.01); *A61K 36/24* (2013.01); *A61K 36/29* (2013.01); *A61K 36/48* (2013.01); *A61K 36/482* (2013.01); *A61K 36/59* (2013.01); *A61K 36/74* (2013.01); *A61K 36/888* (2013.01); *A61K 9/0056* (2013.01)

(58) Field of Classification Search
CPC ....................................................... A61K 36/00
USPC ......................................................... 424/725
See application file for complete search history.

(56) References Cited

U.S. PATENT DOCUMENTS

| | | | |
|---|---|---|---|
| 4,582,705 | A | 4/1986 | Primes et al. |
| 2004/0022880 | A1 | 2/2004 | Shi |
| 2006/0141069 | A1 | 6/2006 | Pushpangadan et al. |
| 2006/0269567 | A1 | 11/2006 | Yuen |
| 2010/0178367 | A1 | 7/2010 | Saxena |

FOREIGN PATENT DOCUMENTS

| | | |
|---|---|---|
| EP | 0890360 A1 | 1/1999 |
| EP | 2184069 A1 | 5/2010 |
| WO | 2005030232 A2 | 4/2005 |
| WO | 2007093897 A2 | 8/2007 |

OTHER PUBLICATIONS

International Search Report mailed Apr. 11, 2012 corresponding to International Application No. PCT/IN2011/000744.
Chaturvedi S et al., "Effect of 'Liver-Kidney Care' an Ayurvedic formulation in cases of various liver and kidney disorders", Medicinal & Aromatic Plants Abstracts, Scientific Publishers, Scientific Publishers, New Delhi—India, vol. 25, No. 2, Apr. 1, 2003.

*Primary Examiner* — Michael Meller
(74) *Attorney, Agent, or Firm* — Ladas & Parry LLP

(57) ABSTRACT

The present invention provides a non-parenteral and non-ocular herbal synergistic detoxifier composition effective for blood purification, blood detoxification and in the treatment and management of disorders related to accumulation of toxins in the body having synergistic effect of its components in specific ratio, better bio availability wherein the amount of dose administered is remarkably low. The formulation of synergistic herbal composition has better patient compliance in the terms of palatability, ease of administration and is formulated in the form of syrup, lozenges/candies/jujubs/mouth freshener, sub-lingual tablets or chewable tablets. The present invention also provides a method of preparation of this formulation.

12 Claims, 7 Drawing Sheets

| Name of Brand | NO (% Inhibition) | Superoxide anion radical (%Inhibition) | Metal chelating activity (%) | Free radical scavenging activity (%DPPH activity) | Hydroxyl radical scavenging assay (% Inhibition of DNA damage) | Total Polyphenols mg GAE/g | Total Flavonoids µg QE/g |
|---|---|---|---|---|---|---|---|
| Active Dabur syrup | 48.40% | 73.34% | 7.06% | 62.07% | 57.80% | 57.15 | 9.94 |
| Baidyanath Raktashodhak vati | 0 | 68.49% | 24.40% | 42.40% | 57.94% | 75.39 | 9.95 |
| Hamdard Safi syrup | 46.66% | 82.23% | 52.01% | 36.31% | 74.87% | 83.90 | 9.18 |
| Himalaya Purim tablets | 19.63% | 50.08% | 42.34% | 38.64% | 75.93% | 92.52 | 10.21 |
| Himani Lalima syrup | 23.52% | 70.27% | 23.59% | 18.78% | 70.50% | 48.64 | 5.48 |
| One of the embodiments of current invention | 51.14% | 83.52% | 59.24% | 62.43% | 76.46% | 93.63 | 10.33 |
| Preferred Embodiment of current invention | 65.30% | 89.20% | 67.30% | 74.10% | 85.90% | 94.12% | 11.23 |

TABLE 1
FIG. 1

| Ingredient | Solubility % in different pH | | | | Metal chelation at different pH | | | | DPPH radical scavenging activity at different pH | | | |
|---|---|---|---|---|---|---|---|---|---|---|---|---|
| | Stomach | | Saliva/Mouth | | | | | | | | | |
| Individual Ingredient | pH 1 | pH 4 | pH 5.5 | pH 6.9 | pH 1 | pH 4 | pH 5.5 | pH 6.9 | pH 1 | pH 4 | pH 5.5 | pH 6.9 |
| Echinacea purpurea leaves ext. | 37 | 39 | 40 | 40 | 42.43 | 42.99 | 55.50 | 45.50 | 54.23 | 53.11 | 55.00 | 55.13 |
| Andrographis paniculata leaves ext. | 35 | 36 | 37 | 38 | 40.21 | 42.22 | 43.00 | 48.67 | 25.78 | 23.96 | 25.31 | 28.13 |
| Boerhaavia diffusa whole plant ext. | 23 | 23 | 23 | 24 | 27.15 | 27.58 | 28.33 | 29.75 | 30.54 | 30.99 | 31.02 | 32.56 |
| Arctium lappa root extract | 17 | 18 | 20 | 18 | 31.32 | 33.45 | 30.21 | 34.78 | 42.15 | 42.61 | 43.85 | 43.21 |
| Rubia cordifolia root ext. | 31 | 29 | 33 | 34 | 20.87 | 42.56 | 48.42 | 48.99 | 10.21 | 15.46 | 20.84 | 33.19 |
| Jacaranda mimosifolia stem | 15 | 16 | 16 | 18 | 17.87 | 18.90 | 19.51 | 21.34 | 19.90 | 20.26 | 20.65 | 21.44 |
| Pothos aureus stem | 16 | 16 | 17 | 17 | 16.91 | 17.88 | 18.93 | 19.45 | 15.26 | 15.77 | 16.30 | 17.98 |
| Ixora coccinea leaves | 13 | 13 | 14 | 16 | 19.23 | 20.21 | 20.96 | 21.30 | 18.89 | 19.76 | 20.22 | 20.98 |
| Hemidesmus indicus roots | 17 | 18 | 18 | 19 | 32.15 | 32.61 | 33.85 | 33.21 | 21.32 | 23.45 | 20.21 | 24.78 |
| Acacia catechu heart wood | 17 | 18 | 17 | 19 | 11.21 | 25.46 | 30.84 | 43.19 | 26.21 | 35.26 | 36.54 | 38.21 |
| Cassia biflora stem | 19 | 19 | 19 | 20 | 21.10 | 22.61 | 23.90 | 24.24 | 23.14 | 23.98 | 24.09 | 24.77 |
| Cassia seamia leaves | 20 | 20 | 20 | 21 | 21.10 | 22.61 | 23.90 | 24.24 | 23.14 | 23.98 | 24.09 | 24.77 |
| Dahlia pinnata flowers | 22 | 23 | 23 | 24 | 25.28 | 25.50 | 25.95 | 27.80 | 18.90 | 19.26 | 19.55 | 20.08 |

TABLE 2

FIG 3A

| Ingredient | Solubility % in different pH | | | | Metal chelation at different pH | | | | DPPH radical scavenging activity at different pH | | | |
|---|---|---|---|---|---|---|---|---|---|---|---|---|
| | Stomach | | Saliva/Mouth | | | | | | | | | |
| Individual Ingredient | pH 1 | pH 4 | pH 5.5 | pH 6.9 | pH 1 | pH 4 | pH 5.5 | pH 6.9 | pH 1 | pH 4 | pH 5.5 | pH 6.9 |
| Example/Formulation I (Normal) | 34 | 35 | 32 | 36 | 26.24 | 26.52 | 27.74 | 27.29 | 31.54 | 30.02 | 32.04 | 32.56 |
| Example/Formulation I (Bioenhanced by Tinospora + Berberis) | 48 | 49 | 49 | 50 | 42.65 | 43.85 | 43.71 | 45.31 | 47.25 | 47.54 | 48.36 | 48.0 |
| Average enhancement by Tinospora + Berberis | 14.75% (Range : 14%-17%) | | | | 16.90% (Range : 15.90%-18.02%) | | | | 16.25% (Range : 15.44%-17.52%) | | | |
| Example/Formulation I Bioenhanced with PEG 400 | 47 | 46 | 52 | 51 | 36.22 | 36.67 | 38.84 | 38.11 | 41.0 | 39.45 | 42.12 | 43.35 |
| Average enhancement by PEG 400 | 15.50% (Range : 13%-20%) | | | | 10.34% (Range : 9.28%-11.10%) | | | | 9.94% (Range : 9.43%-10.79%) | | | |

TABLE 3
FIG. 3B

| Ingredient | Solubility % in different pH | | | | Metal chelation at different pH | | | | DPPH radical scavenging activity at different pH | | | |
|---|---|---|---|---|---|---|---|---|---|---|---|---|
| | Stomach | | Saliva/Mouth | | | | | | | | | |
| Individual Ingredient | pH 1 | pH 4 | pH 5.5 | pH 6.9 | pH 1 | pH 4 | pH 5.5 | pH 6.9 | pH 1 | pH 4 | pH 5.5 | pH 6.9 |
| Example/Formulation II (Normal) | 23 | 24 | 26 | 26 | 31.26 | 31.25 | 32.05 | 32.89 | 26.11 | 26.32 | 27.34 | 27.89 |
| Example/Formulation II (Bioenhanced) by Tinospora + Berberis | 32 | 33 | 35 | 35 | 39.45 | 40.23 | 40.15 | 42.19 | 34.28 | 34.57 | 36.78 | 35.99 |
| Average enhancement by Tinospora + Berberis | 9% (Range :9%) | | | | 11.60% (Range :10.69%-12.39%) | | | | 8.49% (Range :8.1%-9.44%) | | | |
| Example/Formulation II Bioenhanced with PEG 400 | 31 | 34 | 35 | 36 | 35.24 | 35.64 | 39.84 | 40.14 | 29.0 | 29.45 | 30.12 | 30.35 |
| Average enhancement by PEG 400 | 9.25% (Range : 8-10%) | | | | 5.85% (Range :3.98%-7.79%) | | | | 2.82% (Range :2.46%-3.13%) | | | |

TABLE 4
FIG. 3C

| Ingredient | Solubility % in different pH | | | | Metal chelation at different pH | | | | DPPH radical scavenging activity at different pH | | | |
|---|---|---|---|---|---|---|---|---|---|---|---|---|
| | Stomach | | Saliva/Mouth | | | | | | | | | |
| Individual Ingredient | pH 1 | pH 4 | pH 5.5 | pH 6.9 | pH 1 | pH 4 | pH 5.5 | pH 6.9 | pH 1 | pH 4 | pH 5.5 | pH 6.9 |
| Example/Formulation III (Normal) | 21 | 26 | 27 | 27 | 29.31 | 29.48 | 30.56 | 30.51 | 21.20 | 21.58 | 22.54 | 22.07 |
| Example/Formulation III (Bioenhanced) | 37 | 37 | 38 | 39 | 41.15 | 41.87 | 41.25 | 42.00 | 32.15 | 32.45 | 32.89 | 32.00 |
| Average enhancement by Tinospora + Berberis | 12.50% (Range : 11%-16%) | | | | 11.60% (Range : 10.69%-12.39%) | | | | 10.35% (Range : 9.93%-10.87%) | | | |
| Example/Formulation III Bioenhanced with PEG 400 | 37 | 38 | 39 | 40 | 36.21 | 37.56 | 36.78 | 38.45 | 34.22 | 24.35 | 25.12 | 26.78 |
| Average enhancement by PEG 400 | 13.25% (Range : 12%-16%) | | | | 7.29% (Range : 6.22%-8.08%) | | | | 5.77% (Range : 2.58%-13.02%) | | | |

TABLE 5
FIG. 3D

| Ingredient | Solubility % in different pH | | | | Metal chelation at different pH | | | | DPPH radical scavenging activity at different pH | | | |
|---|---|---|---|---|---|---|---|---|---|---|---|---|
| | Stomach | | Saliva/Mouth | | | | | | | | | |
| Individual Ingredient | pH 1 | pH 4 | pH 5.5 | pH 6.9 | pH 1 | pH 4 | pH 5.5 | pH 6.9 | pH 1 | pH 4 | pH 5.5 | pH 6.9 |
| Example/Formulation IV (Normal) | 30 | 29 | 30 | 31 | 26.11 | 26.32 | 27.34 | 27.89 | 17.21 | 17.54 | 18.52 | 18.74 |
| Example/Formulation IV (Bioenhanced) | 45 | 46 | 43 | 46 | 34.21 | 34.58 | 36.78 | 36.99 | 24.56 | 25.65 | 26.38 | 27.00 |
| Average enhancement by Tinospora + Berberis | 15% (Range : 13%-17%) | | | | 8.73% (Range : 8.1%-9.44%) | | | | 8.18% (Range : 7.35%-9.93%) | | | |
| Example/Formulation IV Bioenhanced with PEG 400 | 43 | 45 | 41 | 45 | 32.11 | 32.58 | 35.89 | 35.66 | 22.14 | 24.56 | 25.34 | 25.68 |
| Average enhancement by PEG 400 | 13.5% (Range : 11%-16%) | | | | 7.15% (Range :6.0%-8.55%) | | | | 6.43% (Range : 4.93%-7.02%) | | | |

TABLE 6
FIG. 3E

| Ingredient | Solubility % in different pH | | | | Metal chelation at different pH | | | | DPPH radical scavenging activity at different pH | | | |
|---|---|---|---|---|---|---|---|---|---|---|---|---|
| | Stomach | | Saliva/Mouth | | | | | | | | | |
| Individual Ingredient | pH 1 | pH 4 | pH 5.5 | pH 6.9 | pH 1 | pH 4 | pH 5.5 | pH 6.9 | pH 1 | pH 4 | pH 5.5 | pH 6.9 |
| Example/Formulation V (Normal) | 28 | 30 | 35 | 34 | 55.21 | 58.51 | 58.31 | 56.00 | 61.49 | 62.54 | 62.21 | 63.54 |
| Example/Formulation V (Bioenhanced) | 43 | 44 | 46 | 45 | 65.65 | 65.34 | 67.33 | 70.00 | 71.56 | 70.62 | 72.02 | 72.89 |
| Average enhancement by Tinospora + Berberis | 11.5% (Range : 11%-15%) | | | | 10.07% (Range : 6.83%-14%) | | | | 9.33% (Range : 8.08%-10.07%) | | | |
| Example/Formulation V Bioenhanced with PEG 400 | 40 | 42 | 44 | 45 | 61.23 | 60.33 | 63.36 | 62.38 | 65.11 | 64.68 | 68.78 | 67.45 |
| Average enhancement by PEG 400 | 11% (Range : 9%-12%) | | | | 4.82% (Range : 1.82%-6.38%) | | | | 4.06% (Range : 2.14%-6.57%) | | | |

TABLE 7
FIG. 3F

| Ingredient | Solubility % in different pH | | | | Metal chelation at different pH | | | | DPPH radical scavenging activity at different pH | | | |
|---|---|---|---|---|---|---|---|---|---|---|---|---|
| | Stomach | | Saliva/Mouth | | | | | | | | | |
| Individual Ingredient | pH 1 | pH 4 | pH 5.5 | pH 6.9 | pH 1 | pH 4 | pH 5.5 | pH 6.9 | pH 1 | pH 4 | pH 5.5 | pH 6.9 |
| Example/Formulation VI (Normal) | 19 | 25 | 27 | 28 | 38.66 | 39.66 | 39 | 40 | 40 | 47 | 33 | 45 |
| Example/Formulation VI (Bioenhanced) | 32 | 35 | 39 | 42 | 45.6 | 46 | 49 | 48 | 44 | 51 | 53.03 | 52.56 |
| Average enhancement by Tinospora + Berberis | 10.5% (Range : 11%-15%) | | | | 11.07% (Range : 6.83%-14%) | | | | 8.33% (Range : 8.08%-10.07%) | | | |
| Example/Formulation V Bioenhanced with PEG 400 | 27 | 29 | 30 | 35 | 41.3 | 43 | 44.08 | 39.28 | 39.9 | 39.5 | 49.5 | 47.55 |
| Average enhancement by PEG 400 | 9% (Range : 8.%-11%) | | | | 4.68% (Range : 1.92%-5.38%) | | | | 4.16% (Range : 1.14%-4.57%) | | | |

TABLE 8
FIG. 3G

| SL.No. | Parameters | Healthy Control | Toxicity Induced Control group | Example 1 treated | Example IV treated | Example V treated | Market Sample D-Brand Safi treated | Market Sample E-Brand Lalima treated |
|---|---|---|---|---|---|---|---|---|
| 1 | SGOT | 67.25±3.18 | 170.41±2.81*** | 89.53±9.75 | 106.38±11.06* | 84.8±11.88* | 94.2±22.34*** | 94.1±10.61*** |
| 2 | SGPT | 50.83±1.83 | 195.1±13.39*** | 88.12±3.51*** | 107.84±6.17*** | 66.7±14.57* | 94.7±4.1*** | 91.15±2.9*** |
| 3 | Creatinine | 0.39±0.05 | 1.01±0.02*** | 0.62±0.06 | 0.49±0.09*** | 0.43±0.01*** | 0.51±0.01*** | 0.46±0.06*** |
| 4 | TSH | 0.2±0.02 | 0.98±0.06*** | 0.39±0.05* | 0.48±0.03*** | 0.16±0.01*** | 0.80±0.07*** | 0.55±0.04*** |
| 5 | GSH | 5.62±0.71 | 1.18±0.08*** | 2.3±0.27*** | 2.59±0.22*** | 4.43±0.30*** | 3.93±0.26*** | 3.64±0.19*** |
| 6 | MDA | 1.81±0.25 | 4.52±0.59*** | 3.0±0.35** | 3.71±0.09* | 2.47±0.03*** | 2.90±0.06* | 4.13±0.87ns |
| 7 | GPx | 9.89±0.47 | 3.17±1.02*** | 4.48±0.52* | 4.83±0.43*** | 6.29±0.25*** | 5.29±0.25*** | 4.38±0.20** |
| 8 | NO | 4.18±0.09 | 23.64±0.69*** | 16.92±2.12 | 18.26±0.22*** | 13.07±0.07** | 13.72±0.69*** | 14.18±0.25*** |
| 9 | GR | 48.34±4.35 | 7.92±0.71*** | 11.52±1.42 ns | 11.4±1.64ns | 38.4±3.84*** | 29.49±5.75*** | 19.27±1.20*** |

Table 9

FIG 4

DETOXIFIER HERBAL FORMULATION

This application is a 371 of PCT/IN2011/000744 filed on Oct. 25, 2011, which is incorporated herein by reference.

FIELD OF INVENTION

The embodiments herein generally relates to a synergistic herbal composition and more specifically to a synergistic herbal detoxifier composition for use in human body. The synergistic herbal detoxifier composition is provided as a novel drug delivery based non parenteral and non ocular synergistic herbal composition for buccal, mucosal, sub lingual or oral delivery. The herbal formulation is found to be effective for blood purification including blood detoxification and for use in the treatment and management of disorders related to accumulation of toxins in the body which results in lowering of immune system and relieving stress. The present invention also provided a method of preparation of this formulation.

BACKGROUND OF THE INVENTION

Toxins may be defined as substances which produce physical, emotional, and psychological imbalances in an individual. In modern time the concept of natural cleansing and detoxification of human body is in lime light as the society has increasingly been exposed to toxic compounds such as those present in air, water and foods. Even the beauty and personal care products we use include harmful substances such as petroleum, chemicals and various other toxins. Further most of the foods we eat are produced by using artificial hormones, insecticides and other chemicals which destroy vitamins and essential nutrition and can cause toxin formation in our body. Cigarette smoke, alcohol, different medication, drugs are also examples of toxic sources and it has become apparent that our ability to detoxify substance to which we are exposed is of critical importance to our overall health and to avoid multiple complications. Toxins can also be generated within the body from viral, bacterial or fungal infections (as in the case of candidiasis) and other illnesses which also impact the immune system. Further, toxin and hormones generated as a result of stress and negative mental attitude of urban life style are pressing liver and kidney to such an extent that such organs can not cope with the ever increasing load of toxins. Toxins can damage the body in insidious and cumulative ways by affecting the immune system.

Poor diet, junk food, alcohol, medication, overall poor health of the body and its organs and environmental toxicity all help to contribute to the excessive amount of toxins in the body, which are in general play a major role to cause stress and other life style disorders.

The World Health Organisation (WHO) has warned that more than 270 million people are susceptible of falling victim to diseases linked to unhealthy lifestyles. Over-the-counter, prescriptions, and recreational (illicit) drugs complete the picture, taxing the human body beyond its natural capabilities of detoxification.

The body works tirelessly to naturally remove toxins through our urine, sweat and stools. However, these toxins can be built up in the body to harmful levels which increases the chance of illnesses from minor, major to critical one. Toxins begin to affect the functioning of our body, especially the functioning of vital organ like the liver, kidney and brain.

In an attempt to detoxify bodily toxin, U.S. Patent application No. 2006/0269567 provides an universal detoxifying composition based on Chinese medicines comprising extracts of various herbs such as *Radix Rehmannica, Scutellariae Racis, Rhei Rhizoma, Mirabilite Pawde, Herba Taraxaci, Herba Violae, Puemariae Radix, Fructus Viticis, Fructus Forsythiae, Gardeniae Fructus, Sophara Flavescens Aiton*, in the form of a water tonic or pill for the prevention and treatment of cancer.

In another attempt, U.S. Pat. No. 4,582,705 provides a composition for detoxification for chronic alcoholics and hard line drug addicts which may not be useful for removal or detoxification of regularly generated bodily toxins.

Both the above mentioned document are aimed at overcoming acute intoxicated or disease condition and no attempt is given to tackle toxin generated on daily basis or toxins resulted our living style, environment, genetic predisposition and emotional pattern. This toxin in turn acts as underlying problem for other ensuing diseases or ailments in terms of non-specific illness such as fatigue, headaches, insomnia, bad breath, muscle stiffness, depression, allergies, etc and specific-illness such as migraine, arthritis, psoriasis, influenza, sinusitis, immune deficiencies, tumors.

In this respect, currently available forms of herbal detoxifiers includes syrup, tonic, tablet, capsules such as formulation of Neem & Manjistha commercially available as Active Dabur syrup, a formulation of Anantmool (*Hemidesmus indica*), Haritaki (*Terminalia chebula*), Chirayata (*Swertia chirata*), Kalmegh (*Anchrographic paniculata*), Rewachini (*Rheum emodi*), Amaltas (*Cassia fistula*) and honey available as Baidyanath Raktashodhak vati, a formulation of *Cassia angustifolia, Sphaeranthus indicus* and *Rosa damascena* commerically available as Hamdard Safi syrup, a formulation of *Cassia fistula, Psoralea corylifolia), Saussurea lappa, Picrorhiza kurroa, Neem (Azadirachta indica), Gulancha tinospora/Guduchi, Triphala* consisting of Indian gooseberry/Amalaki (*Emblica officinalis*), Chebulic myrobalan (*Terminalia chebula*) and Belleric myrobalan (*Terminalia bellerica*) and Kalamegha (*Andrographis paniculata*) available in the name of Himalaya Purim tablets and Himani Lalima syrup including Triphala, Neem, Bhringaraj, Manjistha and Honey etc.

The majority of the herbs used are essentially known as detoxifying herbs individually in the existing art. When these herbs are used in a composition or made into a formulation, the amounts of individual herbs administered to achieve therapeutic activity are of high threshold. This is because of the fact that such herbs/active ingredients used in the above mentioned formulation do not have any cumulative therapeutic effect/synergistic effect in terms of removing toxins from the body. Further the active ingredients are of bitter taste with extremely low bio-availability profile due their low solubility and as such all of these formulation are have serious patient compliance problems such as bitter taste and less bio-availability. In order to circumvent the low bio-availability issue and achieving desired therapeutic activity, the amount of dosage prescribed for these formulations are substantially high and therefore risk significant side effects.

Further, all such commercially available detoxifiers use honey or sugar component in order to overcome bitter taste to some extent. But such use of sugar contributes significantly in generation of stress and calorie intake of an individual which pose another problem for the patients.

Accordingly, taste masking for these formulations are a technical problem and the ease of administration for herbal detoxifier formulation and to increase their bio-availability is also a challenge to overcome.

Moreover, since all the available detoxifier formulations are taken as traditional medicine, patient need to change their normal habit & keep themselves reminded of schedule of taking medicine and thus these formulation compromise on patient compliance.

Therefore, an alternative treatment in a novel drug delivery form with greater efficacy and bio-availability of active herbal ingredients at a very less quantity for detoxification of human body, through the use of less number of ingredients in a synergistic manner, must be studied and developed. Novel drug delivery strategies have also been instrumental in optimizing efficacy of therapeutic agents by either modulating their physico-chemical and bio-pharmaceutical properties or minimizing/eliminating the side effects associated with them, reducing treatment time thus offering better patient compliance.

Therefore, there is an utmost societal need to develop such composition and formulations which are effective for blood purification, blood detoxification and stress relieving. At the same time there is a need to provide such detoxifier and stress relieving composition in a form that provide better patent compliance and machetes with lifestyles of growing urban population.

OBJECTS OF THE INVENTION

It is an objective of the invention to provide novel synergistic herbal detoxifier composition for blood purification, blood detoxification and to relieve stress.

Another object of the invention is to use minimum number of active ingredients in a synergistic manner and to use least amount of administrable drug for obtaining therapeutic effect of detoxification.

In another object, the invention overcomes the bitter taste of the active ingredients and to make them more palatable.

Still another object of the invention is to increase the bio-availability of the active ingredients.

Another objective of the present invention is to disclose herbal formulations with novel delivery system.

Another object is to disclose compositions and method of manufacture of the said formulations.

Yet another object of the invention is to provide patient compliance matching habit and lifestyle thereby providing ease of administration without much burden on patient to remember schedule of taking medicine.

Yet another objective of present invention is to disclose a formulation with low calorific value.

Another objective of present invention is to disclose herbal synergistic detoxifier formulation in the form of Lozenges/candies/mouth freshener/jujubs/chewing gum/syrup/tablet or candies freshener.

SUMMARY OF THE INVENTION

In view of the forgoing, a synergistic herbal detoxifier composition is provided. The composition include therapeutically effective amount of one or more active ingredient in the form of one or more herbs selected from a group of herbs including *Echinacea purpurea* leaves, *Andrographis paniculata* leaves, *Boerhaavia diffusa* whole plant, *Arctium lappa* root, *Rubia cordifolia* root; effective amount of one or more bio-availability enhancer. The bio-availability enhancer renders high solubility and high bio-availability of the active ingredient in comparison to solubility and bio-availability of the active ingredient alone; The composition is used for buccal, mucosal, sublingual or oral delivery and achieves therapeutic effect in very low amount.

Powder or extract of *Echinacea purpurea* leaves, *Andrographis paniculata* leaves, *Boerhaavia diffusa* whole plant, *Arctium lappa* root may be present in an amount about and *Rubia cordifolia* root may present in an amount about 0.1 mg to 1000 mg per single administrable dose unit.

The bio-availability enhancer may be of herbal origin or chemical origin. The bio-availability enhancer of herbal origin may selected from the group including extract or powder of *Berberis aristata* stem and *Tinospora cordifolia* stem. The bio-availability enhancer of herbal origin may be present in an amount about 0.1 mg to 1000 mg per single administrable dose unit.

The bio-availability enhancer of chemical origin may be selected from the group including glyceryl mono oleate, poly venyl alcohol, Span 80, Tween 80, Tween 20 and PEG 200 to PEG 6000 or a combination thereof. The bio-availability enhancer of herbal origin is present in an amount about 0.2 mg to 2000 mg per single administrable dose unit.

The active ingredient may also be powder or extract of *Pothos aureus*, leaves of *Ixora coccinea*, stems of *Jacaranda mimosifolia*, roots of *Hemidesmus indicus*, heartwood of *Acacia catechu*, stem of *Cassia biflorain*, leaf of *Cassia seamia* and flower of *Dhalia pinnatain* an amount about 0.1 mg to 100 mg per single administrable dose unit or a combination thereof.

The synergistic herbal detoxifier composition may further comprise one ore more of a pharmaceutically acceptable excipient when the synergistic herbal detoxifier composition is formulated into any one ore more of a lozenges, jujubs, chewing gum, effervescent tablet, mouth freshener, tablet, candy or syrup. The composition when formulated may be taste masked and sweetened to exclude bitter or unpleasant taste of the active ingredient. The taste masking and sweetening of the composition is done without effecting much increase in calorific value of the composition. The pharmaceutically acceptable excipient is selected from the group including one or more of a softening agent, one or more of a sweetening agent and one or more of a flavoring agent for taste masking and sweetening of the synegistic herbal detoxifier composition, one or more of a hardening agent, one or more of a binding agent, one or more of a effervescence couple, one or more of a compressible agent and disintegrative agent, one or more of a polymer when a coating and one or more of a filler.

Taste masking and sweetening may be done by use of maltitol and corn syrup. The ratio of maltitol and corn syrup may be about 5:1 to about 50:1, preferably about 20:1.

The composition is formulated in the form of a lozenges or jujubs or chewing gum or candy or mouth freshener.

BRIEF DESCRIPTION OF DRAWINGS

The embodiments herein will be better understood from the following description with reference to the figures and tables in which:

FIG. 1 illustrates Table 1 showing In-vitro tests results of product of invention Vs leading commercial brands.

FIG. 3A through 3G illustrate in table 2 to table 8, the synergistic effect of example/formulation 5 and comparative bio-enhancement by Herbal bio-enhancer and chemical bio-enhancer (PEG 400)

FIG. 4 illustrates a comparative study of Detoxifying Effect of representative formulations of current invention versus Marketed products after toxicity induction with Sodium Nitrite in rat model though Table 8.

DETAILED DESCRIPTION OF THE PREFERRED EMBODIMENT

Figure 2:
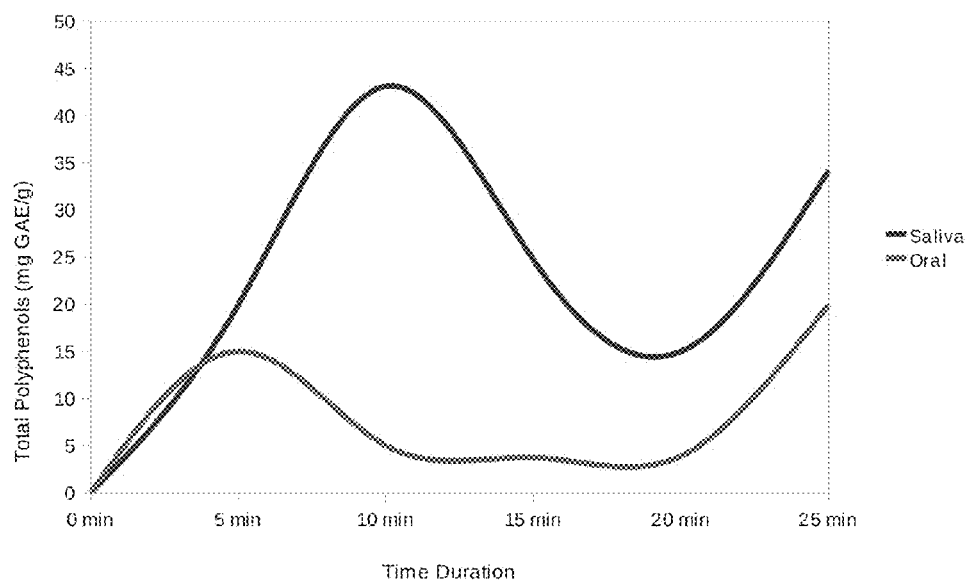
FIG. 2 illustrates a Comparative study of Saliva (Buccal) release of Lozenges/candies/mouth freshener Vs oral intake in-vitro.

The embodiments herein and the various features and advantageous details thereof are explained more fully with reference to the non-limiting embodiments that are illustrated in the accompanying figures & tables and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein. The present invention describes novel synergistic herbal detoxifier composition, their novel delivery mechanisms, formulation and process for the preparation of the same in a pharmaceutical acceptable dosage forms for blood purification, blood detoxification and in the treatment and management of disorders related to accumulation of toxins in the body.

The unique combination of herbs chosen for use herein have been found to invigorate blood purification by detoxification in synergistic manner and helps in the treatment and management of disorders related to accumulation of toxins in the body in the form of non-specific illness such as fatigue, headaches, skin disorder-acne/pimples, insomnia, bad breath, muscle stiffness, depression, allergies, etc and specific-illness such as migraine, arthritis, psoriasis, influenza, sinusitis, immune deficiencies, tumors. hypertension, arthritis, diabetes, immunity disorders, strokes, arteriosclerosis and heart ailments can be traced to this one reason.

The composition of the present invention provides synergistic effect of the constituents, improved bio-availability in comparison to pre-established bio-availability recorded in texts, patient compliance in the terms of palatability and ease of administration and is in novel drug delivery form.

In one embodiment, the synergistic herbal detoxifier composition includes one or more active ingredient in the form of one or more herbs, one or more bio-availability enhancer both taken in a specific therapeutically active amount. The herbs are selected from a group including *Echinacea purpurea* leaves, *Andrographis paniculata* leaves, *Boerhaavia diffusa* whole plant, *Arctium lappa* root and *Rubia cordifolia* root. The bio-availability enhancer used in the composition renders high solubility and high bio-availability of the active ingredient in comparison to solubility and bio-availability of the active ingredient alone. The composition is taste masked/sweetened to exclude bitter or unpleasant taste of the herbs. The taste masking/sweetening of said composition is done without increasing calorific value of the composition. The composition, thus obtained is used for buccal, mucosal, sublingual or oral delivery.

According to a preferred embodiment, the active ingredients selected herein above include extract or powder of *Echinacea purpurea* about 0.1% to 10%, *Boerhaavia diffusa* about 0.1% to 10%, *Andrographis paniculata* 0.1% to 10%, *Arctium lappa* about 0.1% to 10% and *Rubia cordifolia* about 0.1% to 10%.

Alternatively according to a preferred embodiment, the active ingredients selected herein above include *Echinacea purpurea* leaves, *Andrographis paniculata* leaves, *Boerhaavia diffusa* whole plant, *Arctium lappa* root and *Rubia cordifolia* root are present in an amount about 0.1 mg to 1000 mg per single administrable dose unit.

According to another embodiment, the bio-availability enhancer is of herbal origin which is selected from the group comprising extract or powder of *Berberis aristata* stem and *Tinospora cordifolia* stem or a combination thereof. Bio enhancer is present in an amount about 0.1 mg to 1000 mg per single administrable dose unit.

In another embodiment, the bio-availability enhancer is of chemical origin which is selected from the group comprising glyceryl mono oleate, poly venyl alcohol, Span 80, Tween 80, Tween 20 and PEG 200 to PEG 6000 or a combination thereof. Synthetic bioenhancer is present in an amount about 0.2 mg to 2000 mg per single administrable dose unit.

Optionally one or more of the active ingredient is stems of *Pothos aureus*, leaves of *Ixora coccinea*, stems of *Jacaranda mimosifolia*, roots of *Hemidesmus indicus*, heartwood of *Acacia catechu*, stem of *Cassia biflora*, leaf of *Cassia seamia* and flower of *Dhalia pinnata* according to an embodiment herein. The *Pothos aureus* may be present in the composition in about 0.1% to 10%, *Ixora coccinea* in about 0.1% to 10%, *Jacaranda mimosifolia* in about 0.1% to 10%, *Hemidesmus indicus* in about 0.1% to 10%. Alternatively one or more of these is present in an amount about 0.1 mg to 1000 mg per single administrable dose unit.

Illustrative Examples of the synergistic herbal detoxifier/Blood purifier composition are as following: In each of the example described hereinafter contains a specific part and amount of herbs in powder or extract form. The constituents are dissolved in amount of water equal to make a solution of 25 mg/ml. 10 ml of this solution is used to make 100 g of batch using sweetening agent, flavoring agent, binding, effervescent or suitable hardening/softening agent depending upon the form in which formulation is to be prepared. Activity of each of the given compositions can be bio-enhanced for enhancement of bio-availability, the active ingredients may also include bio-enhancer of herbal origin and bio-enhancer of chemical origin. The bio-enhancer of herbal origin includes *Berberis aristata* root and *Tinospora cordifolia* stem in an amount about 0.1 to 10 g. The bio-enhancer of chemical origin include PEG 400 in an amount about 0.2 to 20 g per batch of 100 g. Example 1: In one embodiment of a representative composition, the active ingredients may be powder or extract of *Rubia cordifolia* stem, *Hemidesmus indicus* root and *Acacia catechu* heart wood in an amount about 2.5 to 5.0 g per 100 g batch. Example 2: In another embodiment of a representative composition, the active ingredients may be powder or extract of *Rubia cordifolia* stem in an amount about 3.25 g, *Hemidesmus indicus* root in an amount about 3.25 g and *Arctium lappa* root 3.5 g per batch of 100 g. Example 3: In another embodiment of a representative composition, the active ingredients may be powder or extract of *Pothus aureus* stem, *Ixora coccina* leaves and *Jacaranda mimosa* stem in an amount about 2.0 g to 5.0 g or these may be added to any of the given embodiments as additional ingredients. Example 4: According to still another embodiment of a representative composition, the active ingredients may be powder or extract of *Echinacea purpurea* leaves in an amount about 3.25 g, *Andrographis paniculata* leaves in an amount about 3.25 g and *Boerhaavia diffusa* whole plant in an amount about 3.50 g per 100 g batch. Example 5: In one embodiment of a representative composition per 100 g batch, the active ingredients may be powder or extract of *Echinacea purpurea* leaves 2 g±25%, *Andrographis paniculata* leaves 1 g±25%, *Boerhaavia diffusa* whole plant 1 g±25%, *Arctium lappa* root 2 g±25%, *Rubia cordifolia* root 2 g±25%. Example 5: In another embodiment of a representative composition, the active ingredients are powder or extract of *Cassia biflora* stem in an amount 3.25 g±35%, *Cassia seamia* leaves in an amount 3.25 g±35%, *Dahlia pinnata* flowers in an amount 3.50 g±35% or these may be added to any of the given embodiments as additional ingredients.

In another embodiment, when a formulation is prepared in order to taste mask and sweeten to exclude bitter or unpleasant taste of said active ingredient, any or all of the above mentioned exemplified synegistic herbal detoxifier compositions can be formulated into lozenges/jujubs/chewing gum/effervescent tablet/mouth freshener tablet/candy or syrup etc. Accordingly, as mentioned herein before, the synergistic herbal detoxifier composition further comprises one or more of a suitable pharmaceutically acceptable excipient formulated into lozenges/jujubs/chewing gum/effervescent tablet/mouth freshener tablet/candy. The pharmaceutically acceptable excipient is selected from the group comprising one or more of a softening agent, one or more of a sweetening agent and one or more of a flavoring agent for taste masking and sweetening of the synergistic herbal detoxifier composition, one or more of a hardening agent, one or more of a binding agent, one or more of a effervescence couple, one or more of a compressible agent and disintegrative agent when a tablet is prepared, one or more of a polymer when a coating is preferred, one or more of a filler etc.

The softening agent is present in an amount about 1 to 50%. The softening agent used is pectin, gelatin and/or other pharmaceutically acceptable agents or a combination thereof.

The sweetening agent includes 5% to 95% of one or more non calorific value sweetener, however, a high calorific value sweetener may be substituted. The taste masking and sweetening of the synergistic herbal composition is done by use of agents including sweetening agent selected from the group Maltitol, sorbitol, mannitol, maltase, glycerol, corn syrup or combination thereof according an embodiment of the herein. In a preferred embodiment, the ratio of maltitol to corn syrup in the synergistic herbal composition may be in the range of about 5:1 to 50:1, preferably 20:1 and maltitol along with corn syrup may encompass more than 80% of the synergistic composition according to an preferred embodiment herein. Suitable corn syrups as described herein above may include low conversion corn syrup (dextrose equivalent (DE) of 20-38), regular conversion corn syrup (DE of 38-48) and intermediate conversion corn syrup (DE of 48-58). A corn syrup with a DE of about 42 is preferred, according to one embodiment herein. The flavoring agents is present in an amount about 0.01 to 2.5% that include Mint flavor, Lemon flavor, Orange flavor, Betel leaf flavor, Vanilla flavor, Strawberry flavor, Butterscotch flavor, Pineapple flavor, Chocolate flavor, Mango flavor, Banana flavor & Apple flavor.

The hardening agents is present in an amount 1% to 10% and include PEG20000 and/or other pharmaceutically acceptable agents or a combination thereof.

When a tablet is preferred and the synergistic herbal composition is compressed into tablet shape, a compressible agent is incorporated in an pharmaceutically effective amount. The compressible agent include a hydrate, and may be selected from organic compounds such as dextrose monohydrate, maltodextrin, lactose monohydrate, and dextrin, as well as inorganic compounds including dibasic calcium phosphate dihydrate, dibasic sodium phosphate dihydrate, dibasic sodium phosphate heptahydrate, dibasic sodium phosphate dodecahydrate, monobasic sodium phosphate monohydrate, and monobasic sodium phosphate dihydrate. The disintegrative agent portion is taken in a pharmaceutically effective amount is selected from the group consisting of isomalt, dextrose monohydrate, maltodextrin, lactose monohydrate, dextrin, mannitol, lactitol, sorbitol, xylitol, erythritol, sucrose, and lactose. The disintegrative tablet portion may include one or more effervescent couples. The effervescent couple includes one member from the group consisting of sodium bicarbonate, potassium bicarbonate, calcium carbonate, magnesium carbonate, sodium carbonate and one member selected from the group consisting of citric acid, malic acid, fumaric acid, tartaric acid, phosphoric acid, alginic acid according to an embodiment herein. According to another embodiment of the invention, the synergistic herbal composition is compressed into a tablet shape and a suitable binding agents may be added by a person skilled in the art.

The polymer, taken in a pharmaceutically effective amount to be used in the synergistic herbal detoxifier formulation includes one or more of polyoxyethylene sorbitan fatty acid esters, Tweens such as Tween-80, Tween-20, polyethylene glycols, polyoxyethylene stearates, colloidal silicon dioxide, phosphates, sodium dodecyl sulfate, carboxy methyl cellulose calcium, carboxy-methyl cellulose sodium, methyl cellulose, hydroxyethyl cellulose, hydroxypropylcellulose, hydroxy-propylmethyl cellulose phthalate, micro-crystalline cellulose, magnesium aluminum silicate, triethanolamine, polyvinyl alcohol, and polyvinyl-pyrrolidene (PVP) and SPAN-20, SPAN-80, according to an embodiment herein.

The synergistic herbal detoxifier composition may include other conventional ingredients including other fillers which may include water-soluble compressible carbohydrates such as dextrose, sucrose, mannitol, sorbitol, maltitol, xylitol, lactose, and mixtures thereof, other conventional dry binders like polyvinyl pyrrolidone and the like; sweeteners; lubricants, such as magnesium stearate, stearic acid, talc, and waxes; preservatives; flavors; disintegrants, antioxidants; acidulants, such as but not limited to citric acid, malic acid, tartaric acid, ascorbic acid, and fumaric acid; surfactants; suitable demulcents such as methycellulose, hydroxypropyl methyl cellulose, hydroxyethyl cellulose, hydroxypropyl cellulose, carboxymethyl cellulose and mixtures thereof and coloring agents, according to an embodiment herein.

In another embodiment of the synergistic herbal detoxifier composition, the active ingredients may be in a coated form or in sustained release form in the formulation. Suitable coating material may be Hypromellose, Hydroxyethyl cellulose Hydroxyethylmethyl cellulose, Carboxymethylcellulose sodium, Hydroxypropyl cellulose, Polyethylene glycol or Ethylcellulose or the like.

The suitable bases for compressed tablet of the herbal detoxifier formulation in the form of detoxifier Lozenges/candies/mouth freshener include one or more of sucrose and dextrose- or sucrose-modified materials, (maltose-dextrose spheres containing 92% dextrose, 2-5% maltose, and a portion of higher glucose saccharides) according to an embodiment herein.

If a wet granulation step is used, the base for the compressed tablet lozenge may also contain a binder, such as gelatin or polyvinylpyrrolidone.

It is found that accumulation of toxins in our bodies creates free radicals. Free radicals are dysfunctional molecules which have a missing electron. These are highly unstable molecules and in an attempt to regain stability they devour electrons from surrounding molecules. This creates more damaged molecules and in a cascading effect, this leads to damaged cells and this causes degeneration. These toxins gradually form layers around the lysosomes inside the cells. Lysosomes are structures inside the cells that flush out the waste products from the cells. When toxins form coats around these structures, they block the membrane of the lysosomes from performing their natural function. This leads to the build up of toxins and the creation of free radicals.

In the course to remove toxins from the body, chelation, specifically metal chelation is a process in which toxins are detoxified from body wherein a group of chemical or other compounds isolates free radicals in the body to prevent them from causing further damage to other cells. Accordingly toxin accumulation including stress in body result in alteration of biological macromolecules such as lipids, proteins and nucleic acids and is exhibited by change in redox homeostasis. The detoxifying activity/or phenomenon can be measured through inhibition of NO, Superoxide anion radical, Free radical scavenging activity (% DPPH activity), Hydroxyl radical scavenging assay (DNA damage), Total Polyphenols, Total Flavonoids in herbal preparations.

FIG. 1 illustrates Table 1 showing In-vitro tests results of preferred embodiment of product of invention Vs leading commercially available brands. The results obtained herein represents that representative formulation of present invention has substantial superiority in detoxification of bodily toxin at a very less concentration of active ingredients. As mentioned herein above, in a preferred embodiment, the synergistic herbal composition is formulated for buccal/sublingual route. FIG. 2 illustrates a comparative study of Saliva (Buccal) release of Lozenges/candies/mouth freshener Vs oral intake in-vitro. This experiment was carried as described hereinafter. A) Conditions for Saliva (Buccal) release of Lozenges/candies/mouth freshner: Simulated salivary fluid was prepared taking a composition of Simulated Saliva was $KH2PO4$ (12 mM)+NaCl (40 mM)+$CaCl_2$ (1.5 mM)+NaOH (to make pH 6.2). 150 ml of this fluid (Ref: Dr. L. Hughes and A. Gehris: A New Method of Characterizing the Buccal Dissolution of Drugs, Rohm and Haas Research Laboratories, Spring House, Pa., USA). was taken in dissolution apparatus and 37° C. temperature was maintained at 50 RPM. Lozenge (1 g) was dipped and the samples were withdrawn after every 5 minutes. Total duration was 25 minutes. Total polyphenol content (mgGAE/g) of these samples was estimated by UV method (Ref: Singleton, V. L. and J. A. Rossi, Jr. 1965. Am. J. Enol. Vitic. 16:144-158). B) Conditions for oral release of Lozenges/candies/mouth freshner: A phosphate buffer solution (pH-6.8) was prepared (Composition: $KH_2PO_4$ (13.872 g)+$Na_2HPO_4$ (35.084) dissolved in 1000 ml of DD water and pH of 6.8 was maintained by orthophosphoric acid; Ref: Indian Pharmacopoeia, 1996, vol II)). 150 ml of this solution was taken in dissolution apparatus and 37° C. temperature was maintained at 50 RPM. A Lozenge form (1 g) was dipped and the samples were withdrawn after every 5 minutes. Total duration was 25 minutes. Total polyphenol content (mgGAE/g) of these samples was estimated by UV method (Ref: Singleton, V. L. and J. A. Rossi, Jr. 1965. Am. J. Enol. Vitic. 16:144-158). Inference: Recovery of total polyphenols (mg GAE/g) after 10 minutes was >40 mg GAE/g in Saliva or buccal route whereas it was around 5 mg GAE/g by oral route. This shows that absorption of Lozenges/candies/mouth freshener by saliva or buccal route is 7-8 times more as compared to be consumed by oral route as most of the commercial formulations are either syrups or tablets which are taken by oral route. Moreover Lozenges/candies/mouth freshener are always consumed by saliva or buccal cavity. [DPPH: Diphenylpicrylhydrazyl; GAE: Gallic Acid Equivalents; QE: Quercetin Equivalent]. FIG. 3A through 3G illustrate in table 2 to table 9, the synergistic effect of example/formulation 5 and comparative bio-enhancement by Herbal bio-enhancer & chemical bio-enhancer (PEG 400). An Analysis and comparison of the different results obtained herein, such as the individual effect of the active ingredients in terms of their bio-availability in sublingual/buccal/mucosal and oral route, therapeutic activity in terms of improving different pentameters related to detoxification, formulation 5 was found to be most preferred one. It is also found that both combination of *Berberis aristata* root and *Tinospora cordifolia* stem, in a specific weight ratio, functioned as herbal bio-enhancer for the different examples described herein. FIG. 4 illustrates a comparative study of Detoxifying Effect of representative compositions and/or formulations of current invention versus Marketed products after toxicity induction with Sodium Nitrite in rat model though Table 9. It is observed that the hazardous effect of $NaNO_2$ derives from the reaction of nitrites with amines to produce nitrosamines and with amides to produce nitrosamides. The toxic effects of nitrates and nitrites are well documented in mammalians, including impairment of reproductive function, hepatotoxicity and methaemogobenemia, dysregulation of inflammatory responses and tissue. Accordingly, aim of the present investigation was to determine the comparative efficacy of the synergisticaly formulated detoxifying drug formulations at a very low concentration (10 mg/adult/day) example 1 to example V in sodium nitrite toxicity induced rats and its comparison with other marketed drugs D (Safi of Hamdard, 10 ml/adult/day) and E (Lalima of Dabur, 5 g/adult/day). Model induction for drug toxicity: A Total of 21 animals were randomly distributed into seven groups. All animals received sodium nitrite 80 mg/kg body weight twice daily for 15 days except healthy control group. At the end of experiment, blood samples were collected from all groups and extracted plasma for the measurement biochemical and oxidative stress parameters. Biochemical Parameters: SGOT, SGPT and Creatinine were measured according to kit protocol on fully automatic biochemical analyzer. Stress parameter was measured according to Ohkawa et al (1979). Reduced glutathione was measured according to Ellman method (1959) Oxidized glutathione was measured according to Teare J P et al. (1993) Gluathione reducatse and peroxidase were measured according to Goldberg and Spooner (1993) and Paglia and Valentine (1967). The hepatic (SGOT, SGPT) and renal (creatinine) enzymes were found to be increased in sodium nitrite induced group (diseased control) due to harmful effect of nitrite, nitrosamine formation which damage liver and renal cells. The GR, GSH, GPX enzymes activities were significantly improved in the drug treated groups as compared to sodium nitrite toxicity induced group. These glutathione reducatse (GR), glutathione peroxidase (GPx) and reduced glutathione (GSH) are detoxifying enzymes and has important defense mechanism in protecting cell against oxy free radicals. These parameters were found significant improvement in C treated group as compared to other drug treated group. In the data represented in FIG. 4, table 3, All data are Mean±SD. Turkey t-test was performed between control vs toxicity induced group and toxicity induced group vs treated groups. * (highly significant),  (significant), * (significant), ns (not significant) Where TSH; total thiol (mg/dL), GSH; reduced glutathione (mg/dL), MDA; malonaldialdehyde (nmole/ml), GR; glutathione reducatase (Mmole/min/ml), GPX; glutathione peroxidase (Mmole/min/ml). In conclusion this finding showed that C drug formulation is most effective, then is A formulation in comparison to market products. Formulations of current invention have been administered at very low concentration (10 mg/adult/day) and even have superior efficacy in detoxifying liver and kidenyin comparison to D, Safi (10 ml/adult/day) and E, Lalima (5 g/adult/day). Formulations of current invention play a significant role in prevention of hepatic and renal enzyme along with improved the cellular defense system and reduced free radical mediated tissue injury caused by sodium nitrite in rat.

In one embodiment, the process of preparation used for the herbal detoxifier formulation in the form of detoxifier Lozenges/candies/mouth freshener as defined here in below includes the following steps: Step 1: Dissolve 0.1 to 10 mg dry powder/extracts of active ingredient in the form of *Echinacea purpurea* leaves, *Andrographis paniculata* leaves, *Boerhaavia diffusa* whole plant, *Arctium lappa* root and *Rubia cordifolia* root in warm pharmaceutical grade water and stir to dissolve all the active ingredients to obtain a solution. Optionally 0.1 to 10 mg of either or combination of *Pothos aureus*, leaves of *Ixora coccinea*, stems of *Jacaranda mimosifolia*, roots of *Hemidesmus indicus*, heartwood of *Acacia catechu*, stem of *Cassia biflora*, leaf of *Cassia seamia* and flower of *Dhalia pinnata* may also be taken. Step 2: Double filter the above solution and add 5 to 95% of given sugars Maltitol (700±25%)+Corn Syrup (15±15%) in a Stainless steel (SS) flat bottom broad vessel. Step 3: Boil solution of step 2 to get a clear, uniform and transparent semi-liquid form. Step 4: Optionally add PEG 20,000 (2±1%), Sorbitol (1±1.5%), Span (1±0.5%) in another SS vessel and heat at 100-150° C. to melt uniformly. Step 5: Add solution of step 3 and 4 to boil at 250±50° C. and add 0.05±1% desired flavour (preferably Beetel leaf flavor) and coloring agent. Step 6: Optionally the tablets/lozenges formed can be coated using conventionally known technology. Step 7: Fill in the molds. Allow it to cool and then wrap for chewable tablet.

Alternatively the formulation can be made into jujubs/chewing gum/effervescent tablet using optional additives such as 1 to 50% of softening agents like pectin and gelatin, 0.01 to 2.5% of flavoring agents.

Alternatively the formulation can be used direct as oral syrup solution with or without addition of hardening, softening, effervescence agents.

While the present invention has been described in terms of its specific embodiments, certain modification and equivalents will be apparent to those skilled in the art and are intended to be included with in the scope of the present invention. Above disclosure describe a manner and method of making using the invention and sets forth the best mode contemplated by the inventor for carrying out his invention but is not to be construed as limiting. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications and equivalents of the described modes for carrying out the invention that are obvious to those skilled in formulation development or related fields are intended to be within the scope of the invention. The foregoing description of the specific embodiments will so fully reveal the general nature of the embodiments herein that others can, by applying current knowledge, readily modify and/or adapt for various applications such specific embodiments without departing from the generic concept; and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

I claim:

1. An oral solid composition consisting essentially of an *Andrographis paniculata* leaf extract, a *Boerhaavia diffusa* whole plant extract, a bioavailability enhancer selected from the group consisting of glyceryl monooleate, polyvinyl alcohol, sorbitan monooleate, polyethylene glycol monooleate, polyethylene glycol sorbitan monolaurate, and polyethylene glycol, wherein said solid oral composition is formulated as a lozenge, tablet, or capsule.

2. An oral solid composition consisting essentially of an *Andrographis paniculata* leaf extract, a *Boerhaavia diffusa* whole plant extract, an extract or powder of *Berberis aristata* stem, an extract or powder of *Tinospora cordifolia* stem, a bioavailability enhancer selected from the group consisting of glyceryl monooleate, polyvinyl alcohol, sorbitan monooleate, polyethylene glycol monooleate, polyethylene glycol sorbitan monolaurate, and polyethylene glycol, wherein said solid oral composition is formulated as a lozenge, tablet, or capsule.

3. An oral solid composition consisting essentially of an *Andrographis paniculata* leaf extract, a *Boerhaavia diffusa* whole plant extract, a bioavailability enhancer selected from the group consisting of glyceryl monooleate, polyvinyl alcohol, sorbitan monooleate, polyethylene glycol monooleate, polyethylene glycol sorbitan monolaurate, and polyethylene glycol, and one or more pharmaceutically acceptable excipients selected from the group consisting of pectin, gelatin, maltitol, sorbitol, mannitol, maltase, isomalt, glycerol, corn syrup, mint flavor, lemon flavor, orange flavor, betel leaf flavor, vanilla flavor, strawberry flavor, butterscotch flavor, pineapple flavor, chocolate flavor, mango flavor, banana flavor, and apple flavor, sodium bicarbonate, potassium bicarbonate, calcium carbonate, magnesium carbonate, sodium carbonate, citric acid, malic acid, fumaric acid, tartaric acid, phosphoric acid, alginic acid, dextrose monohydrate, maltodextrin, lactose monohydrate, dextrin, dibasic calcium phosphate dihydrate, dibasic sodium phosphate dihydrate, dibasic sodium phosphate heptahydrate, dibasic sodium phosphate dodecahydrate, monobasic sodium phosphate monohydrate, and monobasic sodium phosphate dihydrate, isomalt, dextrose monohydrate, maltodextrin, lactose monohydrate, dextrin, mannitol, lactitol, sorbitol, xylitol, erythritol, sucrose, lactose, polyoxyethylene sorbitan fatty acid esters, polyethylene glycols, polyoxyethylene stearates, colloidal silicon dioxide, phosphates, sodium dodecyl sulfate, carboxymethyl cellulose calcium, carboxymethyl cellulose sodium, methylcellulose, hydroxyethyl cellulose, hydroxypropyl cellulose, hydroxypropylmethyl cellulose, phthalate, micro-crystalline cellulose, magnesium aluminum silicate, triethanolamine, polyvinyl alcohol, polyethylene glycol 20,000, polyvinylpyrrolidene, and sorbitan laurate, and combinations thereof, wherein said solid oral composition is formulated as a lozenge, tablet, or capsule.

4. An oral solid composition consisting essentially of an *Andrographis paniculata* leaf extract, a *Boerhaavia diffusa* whole plant extract, an extract or powder of *Berberis aristata* stem, an extract or powder of *Tinospora cordifolia* stem, a bioavailability enhancer selected from the group consisting of glyceryl monooleate, polyvinyl alcohol, sorbitan monooleate, polyethylene glycol monooleate, polyethylene glycol sorbitan monolaurate, and polyethylene glycol, and one or more pharmaceutically acceptable excipients selected from the group consisting of pectin, gelatin, maltitol, sorbitol, mannitol, maltase, isomalt, glycerol, corn syrup, mint flavor, lemon flavor, orange flavor, betel leaf flavor, vanilla flavor, strawberry flavor, butterscotch flavor, pineapple flavor, chocolate flavor, mango flavor, banana flavor, and apple flavor, sodium bicarbonate, potassium bicarbonate, calcium carbonate, magnesium carbonate, sodium carbonate, citric acid, malic acid, fumaric acid, tartaric acid, phosphoric acid, alginic acid, dextrose monohydrate, maltodextrin, lactose monohydrate, dextrin, dibasic calcium phosphate dihydrate, dibasic sodium phosphate dihydrate, dibasic sodium phosphate heptahydrate, dibasic sodium phosphate dodecahydrate, monobasic sodium phosphate monohydrate, and monobasic sodium phosphate dihydrate, isomalt, dextrose monohydrate, maltodextrin, lactose monohydrate, dextrin, mannitol, lactitol, sorbitol, xylitol, erythritol, sucrose, lactose, polyoxyethylene sorbitan fatty acid esters, polyethylene glycols, polyoxyethylene stearates, colloidal silicon dioxide, phosphates, sodium dodecyl sulfate, carboxymethyl cellulose calcium, carboxymethyl cellulose sodium, methylcellulose, hydroxyethyl cellulose, hydroxypropyl cellulose, hydroxypropylmethyl cellulose, phthalate, micro-crystalline cellulose, magnesium aluminum silicate, triethanolamine, polyvinyl alcohol, polyethylene glycol 20,000, polyvinyl-pyrrolidene, and sorbitan laurate, and combinations thereof, wherein said solid oral composition is formulated as a lozenge, tablet, or capsule.

5. The composition of claim 1, wherein the components of the composition are present in an amount of about 0.1 mg to about 1000 mg.

6. The composition of claim 2, wherein the components of the composition are present in an amount of about 0.1 mg to about 1000 mg.

7. The composition of claim 3, wherein the components of the composition are present in an amount of about 0.1 mg to about 1000 mg.

8. The composition of claim 4, wherein the components of the composition are present in an amount of about 0.1 mg to about 1000 mg.

9. The composition of claim 1, wherein the bioavailability enhancer is present in an amount of about 0.2 mg to about 2000 mg per single administrable dose unit.

10. The composition of claim 2, wherein the bioavailability enhancer is present in an amount of about 0.2 mg to about 2000 mg per single administrable dose unit.

11. The composition of claim 3, wherein the bioavailability enhancer is present in an amount of about 0.2 mg to about 2000 mg per single administrable dose unit.

12. The composition of claim 4, wherein the bioavailability enhancer is present in an amount of about 0.2 mg to about 2000 mg per single administrable dose unit.

* * * * *